United States Patent [19]

Haüpt

[11] Patent Number: 4,506,395

[45] Date of Patent: Mar. 26, 1985

[54] PROSTHETIC FOOT

[75] Inventor: Werner Haüpt, Duderstadt, Fed. Rep. of Germany

[73] Assignee: Otto Bock Orthopädische Industrie KG, Duderstadt, Fed. Rep. of Germany

[21] Appl. No.: 545,731

[22] Filed: Oct. 24, 1983

[30] Foreign Application Priority Data

Mar. 18, 1983 [DE] Fed. Rep. of Germany ....... 3309777

[51] Int. Cl.³ ............................................. A61F 1/08
[52] U.S. Cl. ................................................ 3/6; 3/12
[58] Field of Search ....................... 3/1, 2, 3, 6, 6.1, 7, 3/32

[56] References Cited

U.S. PATENT DOCUMENTS

| 616,873 | 1/1899 | Andrews | 3/6.1 |
| 3,098,239 | 7/1963 | Nader | 3/7 |
| 4,328,594 | 5/1982 | Campbell et al. | 3/7 |

FOREIGN PATENT DOCUMENTS

| 527975 | 6/1931 | Fed. Rep. of Germany | 3/6 |
| 1420627 | 1/1976 | United Kingdom | 3/7 |
| 698619 | 11/1979 | U.S.S.R. | 3/7 |

Primary Examiner—Richard J. Apley
Assistant Examiner—David J. Isabella
Attorney, Agent, or Firm—Michael J. Striker

[57] ABSTRACT

A prosthetic foot includes a core of incompressible material which has a bottom side sloping upwardly from a toe region towards the rear end of the foot, a wedge-shaped heel element which is applied to that bottom side and formed of a soft, resilient material and a casing portion which is made of hard but resilient synthetic plastic material and shaped so as to form a toe region, a sole and a protective casing of the foot prosthesis. The synthetic plastic material of the casing portion forms an envelope completely wrapping the core and the wedge-shaped heel element at the lateral sides thereof.

10 Claims, 2 Drawing Figures

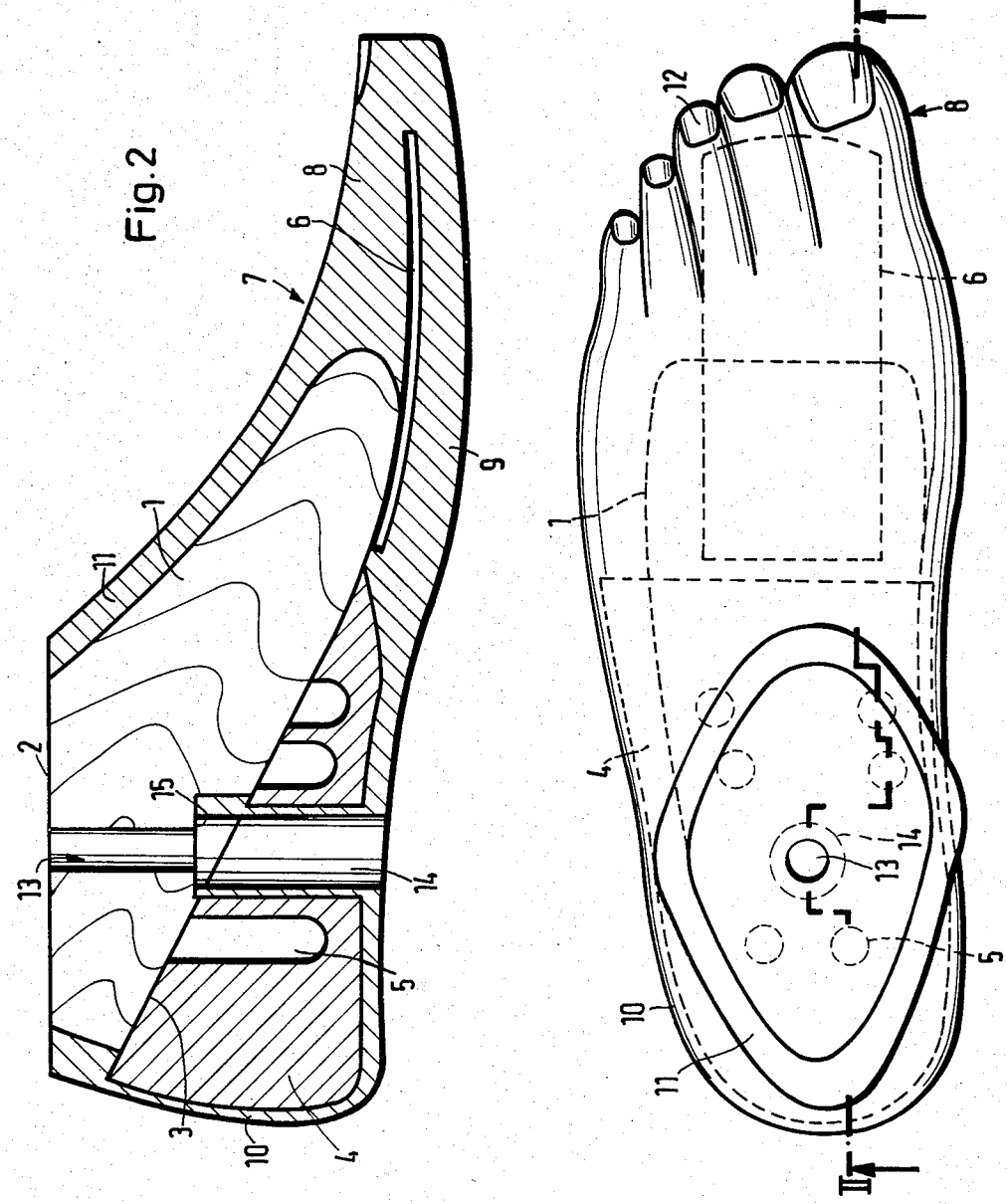

PROSTHETIC FOOT

BACKGROUND OF THE INVENTION

The present invention pertains to a prosthetic foot, which has a core extended in the region of the instep and ankle and an elastic material enclosing the core.

In known prosthetic feet, the core is made of incompressible material and has a sloped bottom side to which a wedge-shaped heel of soft elastic material is attached. A sole of synthetic material with a toe portion is attached to the wedge-shaped heel.

The prosthetic feet, which have no ankle pivot, have been known for years. To achieve a natural walk, despite the lack of the ankle pivot, a prosthetic foot has been suggested, which is composed of several portions. One of the prosthetic feet is disclosed, for example, in U.S. Pat. No. 3,098,239. This known prosthetic foot, namely, the solid ankle-cushion heel prosthetic foot, is comprised of a heel, having a bottom surface sloping forwardly and downwardly from the elevated rear end, an upper foot portion, formed of a tough, but resilient material, and overlying the forward portion and sides of the heel, a horizontal sole portion, formed of resilient material having a density less than that of the upper portion, and a wedge-shaped heel portion of resilient material, having a density less than that of the sole portion. In this known structure, the soft elastic wedge-shaped heel portion serves the purpose of simulating a soft application of the foot and the rolling motion, which in the case of the natural foot are obtained by the ankle pivot.

The synthetic plastic material which forms the wedge-shaped heel portion must be, therefore, sufficiently soft to press the foot in its application and to make the rolling function of the foot possible. On the other hand, this material must be sufficiently hard to ensure a sufficient stability during walking. The sole portion, formed of the hard material, serves for producing the most elastic steps possible, whereas the upper portion is formed substantially of a medium-hard hydrolysis-resistant material and thus must protect the foot structure.

The known construction of the foot prosthesis for simulating a rolling motion has been used and has been further developed without, however, substantial changes. The disadvantage of this known construction is that the wedge-shaped heel portion and the sole are made of an absorbent and porous foam material, through which undesired chemical substances can be sucked when the sole comes in contact with moisture. A user of the prosthetic foot must be always very careful while walking to prevent lowering of the prosthetic foot into the environment which might include moisture and chemical substances. This substantially limits the freedom of walking by the user of the foot prosthesis.

SUMMARY OF THE INVENTION

It is an object of the present invention to provide an improved prosthetic foot.

It is a further object of the invention to provide a foot prosthesis with good walking qualities and which would resist picking up usual chemical substances in a moisture environment by the sole of the prosthesis.

These and other objects of the invention are attained by a prosthetic foot, comprising a core extended in an ankle area and an instep area, and securable to a bone of a user, and formed of incompressible material, said core having a bottom surface sloping substantially rearwardly and upwardly toward a rear end of the foot; a wedge-shaped heel portion attached to said bottom surface and formed of a soft and elastic material; and a casing portion which forms a toe portion and a sole positioned below said heel portion and said core, said casing portion laterally completely covering said heel and said core and being formed of a medium-hard elastic synthetic plastic material, the foot being provided with a vertical step-like bore, for receiving therein means for securing the foot to the bone of the user, said bore extending from an upper surface of said core through said core, said heel portion and said sole, said bore having a portion of enlarged diameter in the region of said heel portion, said enlarged portion being covered with said medium-hard synthetic plastic material of said casing portion so that said casing portion forms a seamless envelope as viewed from said surface.

According to a further feature of the invention, the step-like bore has a shoulder, said shoulder being covered with a sealing washer.

According to the present invention, the medium-hard resilient or elastic material extends to the sole region of the foot and, therefore, the wedge-shaped heel member is enveloped by the medium-hard and hydrolysis-resistant material.

Due to the extension of the elastic material of the sole into the bore portion of the enlarged diameter, it is ensured that no moisture will penetrate into the interior of the wedge-shaped heel member.

Research has been conducted, in which the walking properties of the prosthesis having a sole of a hard, hydrolysis-resistant material, were compared with those of conventional prosthetic feet in which the sole material is softer. It has been further found that certain qualities of the heel member have worsened so much that it was suggested to wrap the heel member with a number of layers of the hydrolysis-resistant hard synthetic plastic material. This proves that the construction of the prosthetic foot according to the invention has comparable walking properties when the wedge-shaped heel portion is formed of the material softer than conventional materials used until now.

By means of the harder sole, and enveloping of the wedge-shaped heel portion, a produced higher hardness can be compensated by an increased softness of the heel portion. Preferably, the heel portion is formed of the extremely soft synthetic plastic material, which is softer than the plastics used for the known prosthetic heel portions, whereby the stability of the prosthesis in the lateral direction is sufficiently ensured by the envelope formed by the hydrolysis-resistant synthetic plastic material. This synthetic plastic material must be preferably somewhat softer than hydrolysis-resistant materials utilized for prosthetic feet until now; this material should be also medium-hard elastic. The prosthesis according to the invention ensures that the rolling properties of the foot in the front region thereof do not worsen, whereas the overall hardness of the toe region is approximately the same as those of conventional prosthetic feet having a two-ply coating of the hydrolysis-resistant plastics and the sole.

This invention offers a two-portion construction of the prosthetic foot, whereas known structures of the prosthesis include at least three portions, namely, the upper portion, the wedge-shaped heel portion and the sole to maintain the required qualities.

It is advantageous that the connection bore formed in the prosthetic foot is in the region of the step or shoulder covered with a sealing washer, which serves for sealing the bore in the upward direction when the screw is inserted into the bore to connect the prosthesis to the human bone.

Since a very large softness is required for the wedge-shaped heel portion according to the invention, it is advantageous that hollows can be formed in the portion.

The wedge-shaped heel portion thus may be provided with at least one hollow for increasing the elasticity of the wedge-shaped heel portion.

The heel portion may be formed with at least one vertical opening which forms said hollow.

The openings in the heel portion may be formed as pockets which open into the core so that the core completely covers said pockets.

The medium-hard elastic material of said casing portion may be a polyurethane foam with the specific weight of about 6 g/cm$^3$.

The soft material of the wedge-shaped heel portion may be VULKOLLAN foam with the specific weight of about 3 g/cm$^3$.

Due to the provision of the hollows in the heel portion, such a degree of softness or elasticity can be obtained which can not be achieved by the selection of the certain material for the heel portion.

Due to the provision of a plurality of the completely closed pockets in the heel portion, a sufficient stability in addition to the necessary softness is attained because the weakened upper side of each open pocket is flat with the bottom side of the core to which the heel portion can be glued.

To obtain a stability of the heel portion in the lateriel directions, the number of the pockets at each side of the heel portion with respect to the central axis thereof may be the same.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWINGS

FIG. 1 is a top plan view of the prosthetic foot according to the invention; and FIG. 2 is a sectional view along line II—II of FIG. 1.

DETAILED DESCRIPTION OF THE PREFERRED EMBODIMENT

With reference to the drawings, the prosthetic foot according to the invention includes a core 1 made of incompressible material, which is wood in the exemplified embodiment. Core 1 has an upper flat connection surface 2, extended in the ankle area and the instep area. The core 1 rises from the toe upwardly towards surface 2. The bottom side 3 of the core slopes generally upwardly from the toe area towards the end of the heel. A wedge-shaped heel segment, or element, encloses the bottom side 3 of the core; the tip of one wedge-shaped heel element extending forwardly towards the toes.

Heel element 4 is formed of a very soft elastic foam material.

A plurality of vertical holes 5, which are shaped as pockets and open into the bottom side of the core 1, are provided in the wedge-shaped heel element. The heel 4 is flatly attached to the bottom side 3 of core 1. In the area of core 1, facing towards the toe region and away from the heel is arranged a flat textile band 6 which is attached to the bottom side 3 of the core and is forwardly protruded therefrom. Band 6 serves in the conventional fashion for reinforcing the front portion of the prosthetic foot and for controlling the rolling function in the front area of the foot.

The whole arrangement composed of core 1, wedge-shaped heel 4 and textile band 6 is totally surrounded by a middle-hard, elastic synthetic plastic material designated by reference numeral 7, which forms a toe region 8, a sole 9, a protective wall 10 for the wedge-shaped heel and a protective wall 11 for the core 1.

The hydrolysis-resistant synthetic plastic material 7, which forms a casing for heel 4, band 6, and core 1, is preferably made of a polyurethane foam with a specific weight of 6 g/cm$^3$, which is close-porous at its outer surface. The thickness of wall 10 and of the portion of sole 9 located below the wedge-shaped heel 4 is very thin and amounts, for example, to 2 mm. This thickness ensures a sufficient elasticity of the wedge-shaped heel segment 4 through the wall 10.

A uniform arrangement of the toe portion 8 and sole 9 makes it possible that the toe portion 8 can be shaped with cosmetic individual toes 12. Such a cosmetic shaping was not possible in conventional prosthetic feet because the sole was always made from the material different from that of the upper portion of the prosthesis, so that a cosmetic shaping of the toe portion 8 was not very suitable.

FIG. 1 illustrates the distribution of pockets 5. In this embodiment an equal number of pockets 5 are provided at each side of the central axis in the lengthwise direction of the prosthesis. The distribution of the hollow pockets in the lengthwise direction results due to the loading points corresponding to the weight distribution during the rolling function of the prosthetic foot.

A vertical bore 13 is provided in the prosthesis, which serves for securing the prosthetic foot to a bone portion (not shown) of a user. Bore 13 extends through the core 1, wedge-shaped heel element 4 and the bottom portion of protective wall 10, which forms the sole 9. Bore 13 has a downwardly extended portion 14 of an enlarged diameter. The stepwise shape of bore 13 forms a shoulder 15. Thereby a screw with the screw head can be inserted from below into the bore 13 through its portion 14 so that the screw head will rest against the shoulder 15. This shoulder can be, preferably during the mounting of the screw (not shown), covered with a sealing washer. The inner surface of the wall forming the enlarged portion 14 is coated with the hydrolysis-resistant synthetic plastic material 7 which merely merges from the sole 9 without any seams into the wall forming the bore portion 14 and extends up to the shoulder 15.

After the application of the prosthetic foot to the bone portion of a user, core 1, wedge-shaped heel 4 and textile band 6, which form the interior of the prosthesis, are hermitically enveloped so that neither moisture nor harmful chemical substances can penetrate into the interior of the foot.

Due to the very soft or elastic arrangement of wedge-shaped heel element and owing to the utilization of the medium-hard hydrolysis-resistant synthesis plastic material 7 for the casing enveloping the core and the heel, the operating characteristics are obtained which are in no way inferior to the conventional prosthetic feet. The prosthetic feet, which have been on the market until now, have the disadvantage that they lack steadiness of the wedge-shaped heel and the sole; this disadvantage is overcome by the present invention.

It is possible that one or more openings 5 for a precise centering of the wedge-shaped heel on the bottom side 3 of core 1 may be utilized. If necessary, core 1 can be also provided with the pockets corresponding to openings or pockets 5. In this case light centering elements can be inserted into the respective pockets.

Openings 5 formed in the wedge-shaped heel element 4 offer a further advantage which resides in that the whole foot prosthesis is lighter as compared with conventional prosthetic feet. The foot prosthesis according to the invention can be made very light. In view of this aspect, the utlization of the core made out of wood is very suitable, since a very light wood, which could be even lighter than a certain synthetic plastic material, may be utilized.

It will be understood that each of the elements described above, or two or more together, may also find a useful application in other types of prosthetic feet differing from the types described above.

While the invention has been illustrated and described as embodied in a foot prosthesis, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A prosthetic foot comprising a core extended in an ankle area and an instep area and securable to a bone of a user, and formed of incompressible material, said core having a bottom surface sloping substantially rearwardly and upwardly toward a rear end of the foot; a wedge-shaped heel element attached to said bottom surface and formed of a soft and elastic material; and a water-resistant casing portion which forms a toe portion and a sole positioned below said heel element and said core, said casing portion laterally completely covering said heel portion and said core and being formed of a medium-hard, elastic synthetic plastic material, the foot being provided with a vertical steplike bore for receiving therein means for securing the foot to the bone of the user, said bore extending from an upper surface of said core through each of said core, said heel element and said sole, said bore having a portion of enlarged diameter in said heel element, walls of said enlarged portion being completely covered with said medium-hard synthetic plastic material of said casing portion so that said casing portion forms a seamless envelope extending out of said bore and completely laterally surrounding said core and said heel element, thereby sealing said foot from moisture and corrosion.

2. The prosthetic foot as defined in claim 1, wherein said steplike bore has a shoulder, said shoulder being covered with a sealing washer.

3. The prosthetic foot as defined in claim 1, wherein said heel element is provided with at least one opening for increasing the elasticity of the wedge-shaped heel.

4. The prosthetic foot as defined in claim 3, wherein said heel element is formed with at least one vertical opening.

5. The prosthetic foot as defined in claim 4, wherein said openings are formed as blend bores which open into the core so that the core completely covers said bores.

6. The prosthetic foot as defined in claim 5, wherein an equal number of said bores are formed at each side of the heel element in the lengthwise direction of the foot.

7. The prosthetic foot as defined in claim 6, wherein the thickness of the casing portion in the region of the heel element amounts approximately to 2 mm.

8. The prosthetic foot as defined in claim 5, wherein said heel element enclosed with said casing portion is formed of a very soft material.

9. The prosthetic foot as defined in claim 8, wherein said medium-hard elastic material of said casing portion is a polyurethane foam with the specific weight of about 6 g/cm$^3$.

10. The prosthetic foot as defined in claim 9, wherein said soft material of the wedge-shaped heel element is a "VULLKOLLAN" foam with the specific weight of about 3 g/cm$^3$.

* * * * *